(12) United States Patent
Mansmann

(10) Patent No.: US 6,629,997 B2
(45) Date of Patent: Oct. 7, 2003

(54) MENISCUS-TYPE IMPLANT WITH HYDROGEL SURFACE REINFORCED BY THREE-DIMENSIONAL MESH

(76) Inventor: Kevin A. Mansmann, 250 W. Lancaster Ave., Suite 310, Paoli, PA (US) 19301

( * ) Notice: Subject to any disclaimer, the term of this patent is extended or adjusted under 35 U.S.C. 154(b) by 0 days.

(21) Appl. No.: 09/818,811

(22) Filed: Mar. 27, 2001

(65) Prior Publication Data

US 2002/0022884 A1 Feb. 21, 2002

Related U.S. Application Data

(60) Provisional application No. 60/192,482, filed on Mar. 27, 2000.

(51) Int. Cl.⁷ .................................................. A61F 2/08
(52) U.S. Cl. .................................................. 623/14.12
(58) Field of Search ......................... 623/11.11, 14.12, 623/16.11, 17.12, 17.16, 18.11, 23.54

(56) References Cited

U.S. PATENT DOCUMENTS

| | | | | |
|---|---|---|---|---|
| 3,867,728 A | * | 2/1975 | Stubstad et al. | 3/1 |
| 3,879,767 A | * | 4/1975 | Stubstad | 3/1 |
| 4,280,233 A | * | 7/1981 | Raab | 3/1.91 |
| 4,502,161 A | * | 3/1985 | Wall | 3/1.91 |
| 4,911,718 A | * | 3/1990 | Lee et al. | 623/17 |
| 4,919,667 A | * | 4/1990 | Richmond | 623/18 |
| 5,067,964 A | * | 11/1991 | Richmond et al. | 623/18 |
| 5,171,322 A | * | 12/1992 | Kenny | 623/18 |
| 5,314,478 A | * | 5/1994 | Oka et al. | 623/18 |
| 5,344,459 A | * | 9/1994 | Swartz | 623/18 |
| 5,578,086 A | * | 11/1996 | Prescott | 623/11 |
| 5,658,343 A | * | 8/1997 | Hauselmann et al. | 623/20 |
| 5,795,353 A | * | 8/1998 | Felt | 623/18 |
| 6,027,744 A | * | 2/2000 | Vacanti et al. | 424/426 |
| 6,187,043 B1 | * | 2/2001 | Ledergerber | 623/8 |
| 6,206,927 B1 | * | 3/2001 | Fell et al. | 623/20.29 |
| 6,231,605 B1 | * | 5/2001 | Ku | 623/11.11 |
| 6,306,169 B1 | * | 10/2001 | Lee et al. | 623/11.11 |

* cited by examiner

Primary Examiner—Bruce Snow
Assistant Examiner—Cheryl Miller
(74) Attorney, Agent, or Firm—Patrick D. Kelly

(57) ABSTRACT

A device for surgical implantation to replace damaged tissue in a joint (such as a meniscus in a knee) is created from a hydrogel that is reinforced by a three-dimensional flexible fibrous mesh. In a meniscal implant, the mesh is exposed at one or more locations around the periphery, to provide anchoring attachments that can be sutured, pinned, or otherwise securely affixed to tissue that surrounds the implant. The fibrous mesh should extend throughout most of the thickness of the hydrogel, to create an "interpenetrating network" (IPN) of fibers modelled after certain types of natural body tissues. Articulating surfaces which will rub and slide against cartilage should be coated with a hydrogel layer that is completely smooth and nonabrasive, and made of a material that remains constantly wet. This composite structure provides a meniscal implant with improved strength, performance, and wettability compared to implants of the prior art. This type of implant may also be useful in repairing other joints, such as shoulders, wrists, ankles, or elbows, and in repairing injured or diseased hands, fingers, feet, or toes.

19 Claims, 1 Drawing Sheet

MENISCUS-TYPE IMPLANT WITH HYDROGEL SURFACE REINFORCED BY THREE-DIMENSIONAL MESH

RELATED APPLICATION

This application claims the benefit under 35 USC §119(e) of a prior U.S. provisional patent application, Ser. No. 60/192,482, filed Mar. 27, 2001.

BACKGROUND OF THE INVENTION

This invention relates to surgical implants that are designed to replace meniscal tissue and possibly cartilage in a mammalian joint, such as a knee.

The structure and components of soft tissues are discussed in nearly any textbook on human physiology (e.g., Guyton and Hall, *Textbook of Medical Physiology*, 9th edition (1996) at page 186). Very briefly, the cells in most types of "soft tissue" (excluding bones, teeth, fingernails, etc.) are held together by a matrix (i.e., a three-dimensional network) of two types of fibers. One type is composed mainly of collagen, a fibrous protein that provides most of the tensile strength of tissue.

The other type of fiber consists mainly of "proteoglycan filaments". These filaments contain a small quantity of protein and a much larger amount (roughly 98%) of hyaluronic acid, a natural polymer with alternating saccharide rings of glucosamine and glucuronate. Unlike collagen fibers, which are thick and provide high levels of tensile strength, proteoglycan filaments are extremely thin, and cannot be seen under light microscopes. They cause the watery extra-cellular fluid in soft tissue to form a gel-like material called "tissue gel". This gel contains water, the proteoglycan filaments, and any other extra-cellular molecules that are suspended in the watery solution.

Roughly ⅙ of the volume of a person's body is made up of tissue gel, and it is essential to proper functioning of any type of soft tissue; among other things, it helps oxygen and nutrients reach cells, it aids in the removal of waste metabolites from tissue, and it helps tissue remain flexible and supple. Because proteoglycan filaments are so thin, molecules dissolved in tissue gel can permeate through the gel material with very little impedance; experiments have indicated that dye molecules can diffuse through tissue gel at rates of about 95 to 99 percent of their diffusion rates in water or saline.

Because nearly any type of soft tissue, in its normal and natural state, can be regarded as a type of hydrogel, many efforts have been made to create and use synthetic polymeric hydrogel materials as tissue implants. Most of these polymers are created by using non-parallel strands of long organic polymeric molecules (usually with chemical structures that are easier to work with and manipulate than glucosamine and glucuronate). Such molecules, to be suitable for use in a hydrogel, must be very hydrophilic (i.e., they must be able to attract and hold large quantities of water). This is most frequently accomplished by polymerizing precursor molecules that will provide large numbers of hydroxy groups (or other hydrophilic groups), on relatively short "side chains" or "side groups" that are bonded in a regular spaced manner to the long "backbone" strands of the final polymer.

An example of a synthetic hydrogel of this nature is PHEMA (an acronym for poly-hydroxy-ethyl-methacrylate), which is used to make soft contact lenses, drug-releasing hydrogels, and similar articles. In contact lenses made of PHEMA, the polymer does not actually bend light. Instead, the water that dwells inside the PHEMA polymer when the lens is hydrated does that job. The hydrophilic PHEMA polymer merely holds water molecules together, in the shape of a contact lens. If a polymer such as PHEMA is dehydrated, it typically becomes brittle; as long as it remains filled with water, it stays soft and flexible. However, like most synthetic hydrogels, PHEMA does not have sufficient strength and durability to last for years (or decades) as a permanent surgical implant.

PHEMA is certainly not the only synthetic polymer used to create biocompatible hydrogels; other polymers that can swell and soften when saturated with water include various hydrophilic polyurethane compositions (e.g., Gorman et al 1998 and U.S. Pat. No. 4,424,305, Gould et al 1984), poly(vinyl alcohol) compositions (e.g., Wang et al 1999), and other compounds known to those skilled in this field of art.

The flexible, pliable, gel-like nature of a synthetic hydrogel (when saturated with water) arises mainly from crosslinking attachments between non-parallel fibers in the gel. Depending on the specific polymeric structure that has been chosen, these crosslinking attachments between the long "backbone" chains in a polymer can be formed by covalent bonding, by hydrogen bonding or similar ionic attraction, or by entangling chains that have relatively long and/or "grabby" side-chains.

Regardless of which type of bonding or entangling method is used to bind the backbone chains together to form a hydrogel, the "coupling" points between molecular chains can usually be flexed, rotated, and stretched.

In addition, it should be recognized that the backbone chains in hydrogel polymers are not straight; instead, because of various aspects of interatomic bonds, they are somewhat kinked, and can be stretched, in an elastic and springy manner, without breaking the bonds.

In a typical hydrogel, the fibers usually take up less than about 10% of the volume; indeed, many hydrogels contain less than 2% fiber volume, while interstitial spaces (i.e., the unoccupied spaces nestled among the three-dimensional network of fibers, which become filled with water when the gel is hydrated) usually make up at least 90 to 95% of the total volume. Accordingly, since the "coupling" point between any two polymeric backbone chains can be rotated and flexed, and since any polymeric backbone molecule can be stretched without breaking it, a supple and resilient gel-like mechanical structure results when a synthetic hydrogel polymer is hydrated.

Various methods are known for creating conventional polymeric hydrogels. A number of such methods involve mixing together and reacting precursor materials (monomers, etc.) while they are suspended in water or other solvent. This step (i.e., reacting two or more monomers while they are suspended in a solvent) gives a desired density and three-dimensional structure to the resulting polymerized strands or fibers. The resulting material is then frozen, to preserve the desired three-dimensional structure of the fibers. The ice (or other frozen solvent) is then vaporized and removed, without going through a liquid stage, by a sublimizing process (also called lyophilizing), using high vacuum and low temperature. After the solvent has been removed, any final steps (such as a final crosslinking reaction and/or rinsing or washing steps, to remove any unreacted monomers, crosslinking agents, quenching agents, etc.) are carried out. The polymer is then gradually warmed up to room temperature, and it is subsequently saturated with water, to form a completed hydrogel.

These and other methods for creating synthetic polymeric hydrogels that are biocompatible and intended for surgical implantation are described in numerous patents, including U.S. Pat. Nos. 3,822,238 (Blair et al 1974), 4,107,121 (Stoy 1978), 4,192,827 (Mueller et al 1980), 4,424,305 (Gould et al 1984), 4,427,808 (Stol et al 1984), and 4,563,490 (Stol et al 1986). In addition, various methods of forming hydrogel coatings on the surfaces of other ("substrate") materials are also described in various patents, such as U.S. Pat. Nos. 4,921,497 (Sulc et al 1990) and 5,688,855 (Stoy et al 1997).

There also have been efforts to reinforce hydrogels with an interpenetrating network (IPN) of fibers to enhance the soft hydrogel's mechanical properties. These fiber reinforcements have been with either chopped or longitudinally aligned fibers within the hydrogel. A number of these efforts to develop "composite hydrogels" apparently have focused on attempts to create synthetic pericardial tissue (i.e., the membrane that surrounds the heart); see, e.g., Blue et al 1991 and Walker et al 1991. Articles which describe these and other efforts to develop "composite" hydrogels are discussed in two review articles, Corkhill et al 1989 and Ambrosio et al 1998. In addition, efforts to develop composite implants with fibers embedded in an "elastomeric matrix", for use in intervertebral discs designed for repairing spinal damage, are described in various patents such as U.S. Pat. No. 4,911,718 (Lee et al 1990) and U.S. Pat. No. 5,171,281 (Parsons et al 1992).

U.S. Pat. No. 5,855,610 (Vacanti et al 1999) also describes an approach to implanting under the skin, in a first location, a flexible porous network that has been seeded with cells, then leaving it there for a number of days to encourage fibrous tissue growth into it, and then removing it and implanting it into a second location. Although that approach is quite different from the subject invention, that patent is worth noting because it contains a very extensive listing of patents and scientific articles in the field of flexible implants.

As used herein, all references to "implants" or "implantation" (and all terms such as surgery, surgical, operation, etc.) refer to surgical or arthroscopic implantation of a reinforced hydrogel device, as disclosed herein, into a mammalian body or limb, such as in a human patient. Arthroscopic methods are regarded herein as a subset of surgical methods, and any reference to surgery, surgical, etc., includes arthroscopic methods and devices. The term "minimally invasive" is also used occasionally herein, even though it is imprecise; one should assume that any surgical operation will be done in a manner that is minimally invasive, in view of the needs of the patient and the goals of the surgeon.

Despite all the efforts cited above (and numerous others in that field, as well), surgically implantable hydrogels that are intended as permanent prosthetic replacements for damaged or diseased tissue suffer from a number of important limitations, including (1) relatively low strength and durability, and (2) difficulties in anchoring them permanently in a desired location, in ways that provide adequate strength. Both of these crucial factors severely limit the number and variety of uses for such hydrogels that have been developed and commercialized to date. In general, they are used today mainly for disposable external use (such as in contact lenses, and in skin patches), and for resorbable devices that will release a desired drug for a prolonged period and then gradually dissolve and disappear inside the body.

By contrast, this primary goal of this invention is to disclose a hydrogel device with a reinforcing mesh embedded in the hydrogel, to help makes the gel device strong enough and durable enough to be surgically implanted in a knee joint, as a replacement for a damaged meniscus.

Meniscal Tissues in Knees

Each knee joint of a human contains a "medial" meniscus, and a "lateral" meniscus. The lateral meniscus is located on the outer side of the leg, directly above the location where the upper end of the fibula bone is coupled to the tibia ("shinbone"). The medial meniscus is located on the inner side of the leg.

Each meniscus (also referred to, especially in older texts, as a "semilunar fibrocartilage") has a wedged shape, somewhat comparable to a segment from an orange or other citric fruit, but with a substantially larger curvature and "arc". The thickest region is around the periphery (which can also be called the circumference, the rim, and similar terms). When implanted into a knee, this peripheral rim normally will be anchored to the surrounding wall of a fibrous "capsule" which encloses the knee joint and holds in the synovial fluid, which lubricates the cartilage surfaces in the knee. The two ends of each semi-circular wedge are coupled, via ligaments, to the "spine" protrusions in the center of the tibial plateau.

The inner edge of a meniscus is the thinnest portion of the wedge; this edge can also be called the apex, the margin, and similar terms. It is not anchored; instead, as the person walks or runs, each meniscus in a knee is somewhat free to move, as it is squeezed between the tibial plateau (beneath it) and a femoral runner (above it). The bottom surface of each meniscus is relatively flat, so it can ride in a relatively stable manner on top of the tibial plateau. The top surface is concave, so it can provide better, more closely conforming support to the rounded edge of the femoral runner. Because of its shape, location, and ability to flex and move somewhat as it is pushed, each meniscus helps support and stabilize the outer edge of a femoral runner, as the femoral runner presses, slides, and "articulates" against the portion of the tibial plateau beneath it.

However, because all four of the menisci inside a person's knees are in high-stress locations, and are subjected to frequently-repeated combinations of compression and tension (and sometimes abrasion as well, especially in people suffering from arthritis or other forms of cartilage damage), meniscal damage often occurs in the knees of humans, and occasionally other large animals.

It should also be noted that, in humans, meniscal-type tissues also exist in shoulder joints and wrist joints.

Various efforts have been made, using prior technology, to repair or replace damaged meniscal tissue. However, because of the complex structures and anchoring involved, and because of the need to create and sustain extremely smooth and constantly wet surfaces on the inner portions of each meniscal wedge, prior methods of replacing or repairing damaged meniscal are not entirely adequate.

Accordingly, one object of this invention is to disclose a hydrogel device, with a reinforcing mesh that helps to make the gel component strong enough and durable enough to be surgically implanted in a knee joint, as a replacement for a damaged meniscus.

Another object of this invention is to disclose a composite meniscal implant having a hydrogel component, with a reinforcing mesh that is: (i) exposed on the outer peripheral surface of the implant, to enable secure anchoring of the meniscal implant around the periphery; and, (ii) hidden and internal on the inner wedge surfaces of the meniscus, so that the hydrogel coating layers will remain completely smooth and will not abrade the cartilage surfaces on the femoral runner and tibial plateau that will rub and articulate against the meniscus.

Another object of this invention is to disclose a composite implant device having a hydrogel component reinforced by a three-dimensional mesh which creates a reinforcing "interpenetrating network" that resembles certain types of natural body tissues, such as interfaces between bone and cartilage.

Another object of this invention is to disclose a surgical implant having a hydrogel component that partially encloses a three-dimensional mesh, and wherein the mesh emerges from one or more selected locations in the implant, to provide improved anchoring capabilities, but wherein the mesh is not exposed on certain other surfaces of the implant, so that a very smooth hydrogel surface will cover those portions of the implant.

Another object of this invention is to disclose a wedge-shaped implant having a smooth inner edge and an outer rim designed for anchoring, which might be useful in some situations where a surgeon must repair a damaged or disease joint other than a knee, such as a shoulder, wrist, ankle or elbow joint, or in an interface between two bones in another part of the body, such as a hand or foot.

These and other objects of the invention will become more apparent through the following summary, drawings, and description of the preferred embodiments.

SUMMARY OF THE INVENTION

A device designed for surgical implantation to replace damaged tissue (such as a meniscus in a knee) is disclosed, having a hydrogel component reinforced by a three-dimensional mesh. The mesh component provides strength and structural support for the implant, which has at least one articulating surface, and at least one anchoring surface. In one embodiment, the mesh emerges from one or more selected locations around the peripheral rim of a meniscal implant, to provide anchoring attachments that can be sutured, pinned, clipped, or otherwise securely affixed to the fibrous capsule that surrounds the knee. Preferably, the rim surface should be porous, to promote scar tissue (or, in some cases, bone tissue) ingrowth into the implant, to create a strong permanent anchoring support for the implant. In addition, at least some portion of the mesh component preferably should extend through most of the thickness of the hydrogel portion, to create a reinforcing "interpenetrating network" (IPN) of fibers, modelled after certain types of natural body tissues. The "articulating" surfaces of a meniscal wedge, which will rub and slide against femoral and tibial cartilage, should be coated with a hydrogel layer which is smooth and nonabrasive, and made of a material that remains constantly wet. This composite structure, with hydrogel layers surrounding an embedded mesh component, provides a joint-repair implant with improved anchoring, strength, and performance compared to implants of the prior art. Because of certain design advantages, this type of implant may also be useful in surgical repair of other joints, such as damaged shoulders, wrists, ankles or elbows, or in surgical repair of feet or hands.

DESCRIPTION OF PREFERRED EMBODIMENTS

Figure 1:
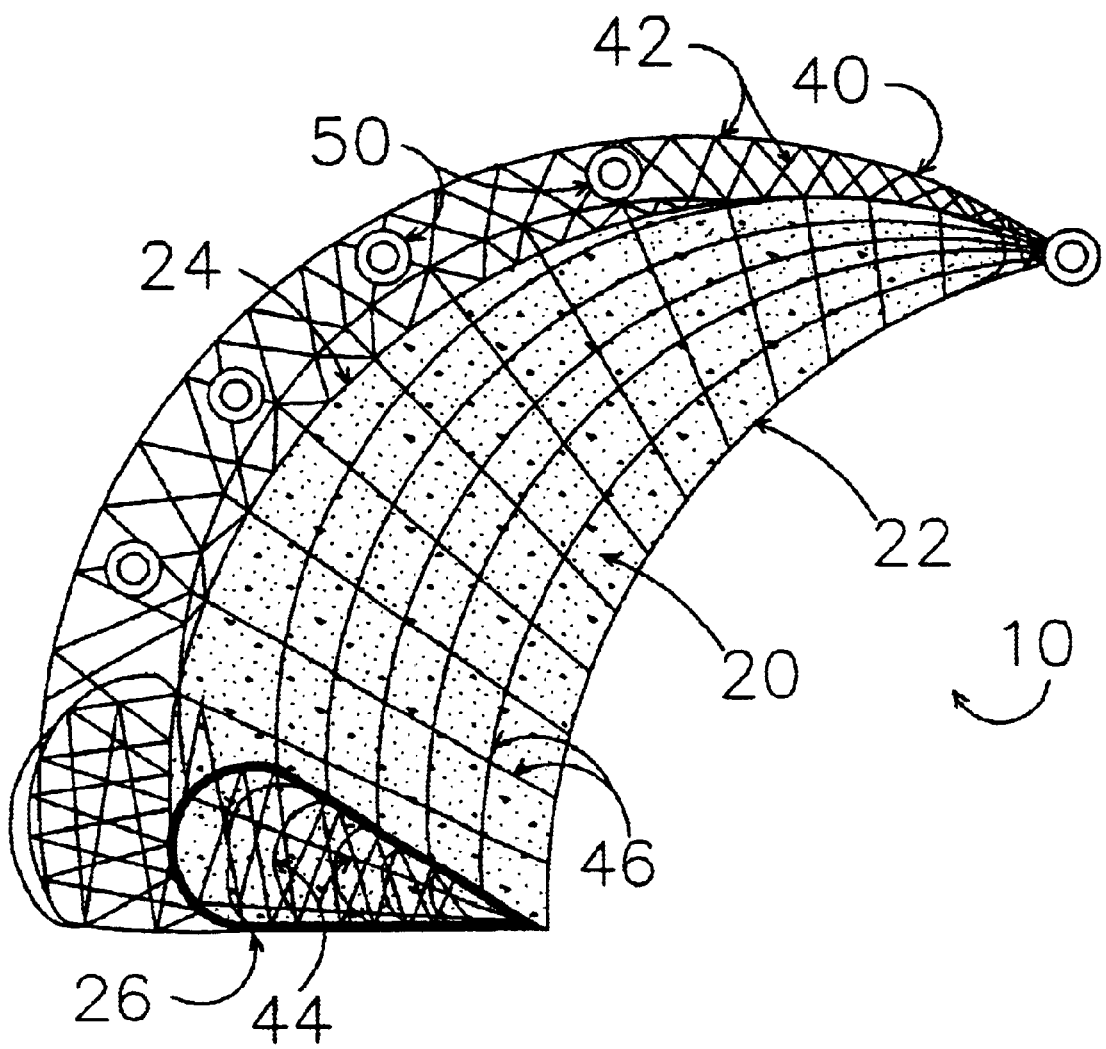
FIG. 1 is a cross-sectional perspective view of a wedge-shaped implant, having an embedded mesh that strengthens and provides anchoring support around the peripheral rim of the implant, and inner surfaces that are covered by a layer of smooth and "lubricious" hydrogel.

A wedge-shaped implant is disclosed herein, with a hydrogel component that provides smooth inner surfaces, and a three-dimensional mesh (which can also be called a network, matrix, or similar terms) that reinforces the hydrogel and provides anchoring attachments around the peripheral rim of the implant. In one preferred embodiment, this implant is designed primarily for surgical implantation in a knee joint, to replace a damaged or diseased meniscus. In alternate embodiments, this type of implant may be adapted (by giving it a different size and/or shape) to render it potentially useful in various types of reconstructive surgery where a surgeon must try to repair another type of joint (such as an ankle or wrist), or some other interface between bones, such as in a foot or hand.

Referring to FIG. 1, item 10 is a perspective view of a wedge-shaped implant, such as an implant to replace a damaged meniscus in a knee joint. The hydrogel component 20 is shown in gray. When seen from above, in a plan view, this hydrogel component 20 has an arc-like or crescent shape, comparable to a curved claw, with an inner surface 22 and a peripheral rim surface 24. When seen from an anterior or posterior direction, it has a wedged cross-sectional shape, shown by cross-section 26. This "wedged arc" shape of hydrogel component 20 emulates the shape of natural meniscus tissue, inside a healthy knee joint.

After implantation, the inner surface 22 of the hydrogel wedge 20 will fit into the gap between a femoral runner (a segment of cartilage at the bottom end of the thigh bone), and a tibial plateau (another segment of cartilage, at the top end of a shinbone). As in a healthy knee, this placement and structure of the hydrogel implant 20 will allow a meniscal implant to help distribute, share, and reduce the compressive loads that are imposed on the femoral and tibial segments of cartilage.

Depending on the condition of a damaged or diseased knee joint, one or two single-compartment implants might be used, in either or both of the medial and/or lateral locations in the knee. Alternately, a two-compartment implant might be used, with two hydrogel compartments that are separate from each other but connected to each other by a bundle, belt, or sheet of the mesh material that is embedded in both of the hydrogel components.

The mesh 40 shown in FIG. 1 is composed of two classes of long fibers: (i) peripheral and/or anchoring strands 42, which extend out of the hydrogel component 20; and, (ii) penetrating strands 44, which enter and pass through some portion of hydrogel component 20. Due to the woven, knitted, or other three-dimensional structure of the mesh, a single long strand in mesh 40 might provide a peripheral/anchoring strand 42 at one location and a penetrating strand 44 at another location.

FIG. 1 also shows fiber strands 46 on the interior surface of the hydrogel wedge. In a properly designed meniscal implant, the inner surfaces need to be completely smooth, to avoid and minimize any risk of abrasion of the cartilage surfaces on the femoral runners and tibial plateau. Accordingly, strands 46 should be regarded as being for illustration only, to clearly indicate that the mesh should extend through essentially the entire hydrogel component, while a relatively thin (and potentially transparent or semi-transparent) layer of hydrogel material covers the embedded mesh on any "articulating" surfaces (i.e., surfaces that will rub against a native cartilage surface, inside the joint).

If desired, the outermost layer of the hydrogel, on one or more surface areas of the implant, may be made of a material that is different from the interior gel material. This can, for example, allow the inner portion of the hydrogel material (or an elastomeric material which does not retain water molecules, and which therefore is not classified as a hydrogel) to be selected for high strength, while the outermost layer is made of a different or modified hydrogel material that is selected and designed to be highly "lubricious".

As used herein, the term "lubricious" indicates that the surface of an implant, in a certain area, will remain constantly wet. This trait can be provided by means known to those skilled in the art. As one example, a lubricious surface can be provided by a hydrophilic polymeric material with opencell pores on its surfaces; such pores can be provided by various means, either by proper selection and treatment of the monomers that will form a polymer, or by molding a polymeric material that has forced into a layer of granules (such as granules of salt, sugar, or similar material) that can be dissolved by water or other suitable solvent that will not damage the polymer, thereby allowing the granules to be completely removed and rinsed out after the polymer has fully set. As another example, the surface layer of a polymer can be provided with numerous hydrophilic molecular groups that are exposed and accessible to water molecules, on the surface of the outer layer of a synthetic polymer. In general, lubricious hydrogel materials tend to be softer and more flexible than either: (i) hydrogel materials that are selected for greater strength, since greater strength and durability typically require and imply higher levels of hardness, stiffness, etc.; and/or (ii) other elastomeric materials which contain no water molecules (and therefore are not regarded as "gels"), but which might provide a well-suited "substrate" or "foundation" surface that can securely support a hydrogel material bonded to it.

In addition, if two different types of hydrogel material are used (or if a layer of hydrogel is used to coat a segment of elastomeric material which is not a hydrogel), it is possible to provide a non-planar interface between the softer material and the stiffer material, to provide greater strength to the interface between them, and better reinforcement for the hydrogel layer. This type of non-planar interface is described in greater detail in provisional patent application No. 60/250,091, filed in November 2000, entitled "Multi-Perforated Non-Planar Device for Anchoring Cartilage Implants and High-Gradient Interfaces". A copy of the text of that provisional application is included with this utility application, so that it will be fully included in the file wrapper of this application. The contents of that provisional application are incorporated herein by reference, as though fully set forth herein.

In addition to the explicit teachings in application 60/250,091, it also should be recognized that the type of multi-perforated non-planar interface layer disclosed therein can be provided by means of a slice of an open-cell foam, if the foam has a suitable average pore size, and if the slice has a suitable thickness.

In addition, it also should be recognized that a "mesh" component, as that term is used herein, can be provided by a slice (which may be a wedge-shaped slice, if desired) of an open-cell foam, provided that the foam has a suitable average pore size, and the slice has a suitable thickness, so that both physical traits, working together, establish a mesh-type structure which will provide suitable strengthening and reinforcing for a hydrogel component, in the types of implant disclosed herein.

FIG. 1 also illustrates five anchoring reinforcements 50, located around the periphery of the mesh 40. In one preferred embodiment, these can be made of the same stranded material that makes the mesh, in a manner comparable to sewing or weaving a buttonhole using the same type of thread that is used to sew a garment together. Alternately, these can be made of a molded or machined material, such as a biocompatible plastic or metal. Since anchoring reinforcements 50 will be positioned away from any articulating cartilage surfaces, they can be designed for strength and convenience, and do not have to be perfectly flat or smooth.

In the discussion herein, it is assumed that the mesh will extend outside of the hydrogel or elastomer material, around the periphery of the implant. However, alternate designs can be tested and used, if hydrogel implants having protruding fibers suffer from cutting or other damage to the hydrogel component, around the periphery. As one example, a series of reinforced eyelets can be embedded inside the hydrogel, around its periphery, and suture material can be passed through the hydrogel and through the eyelets, by the surgeon doing the operation. As another example, a tough elastomeric material made of an entirely synthetic polymer (which will not be classified as a hydrogel, if the polymeric material does not trap and retain water molecules) can be used to provide the peripheral rim surface of an implant, from which the reinforcing fibers will emerge.

Regardless of whether the mesh component extends beyond the peripheral rim of an implant, the peripheral rim of the implant can be provided with a porous outer layer of hydrogel or elastomeric material, to promote tissue ingrowth into the porous rim region of the implant. This type of porous layer in a hydrogel or elastomer can be done by steps such as using a layer of salt, sugar, or other granular compound (or "intercalating" fibers or other material, such as a wax-like material that can be melted and/or vaporized at a temperature that will not damage the gel or elastomer) during the processing step that is used to mold the gel or elastomer in the rim area. Alternately, methods comparable to surface etching, using acids or other chemicals, laser beams or other types of radiation, etc., may be useful, depending on the type of hydrogel or elastomeric material being treated.

Methods of Manufacture

Any of at least four (and possibly more) alternative approaches can be used to manufacture the three-dimensional mesh which will be used to reinforce the hydrogel portion of an implant as disclosed herein. Each approach is discussed separately, below.

The first approach involves weaving, knitting, or other physical interlacing of pre-existing fibers. The second approach involves crosslinking, gluing, or similar chemical treatment of pre-existing fibers. The third approach involves molding a suitable pre-polymeric compound into a shape which directly provides the desired mesh structure. The fourth approach involves using a slice of an open-cell foam. If desired, various combinations of those approaches can be used.

With regard to the first approach, the term "woven" is used broadly herein, and includes three-dimensional structures created from continuous fibers which are interlaced or otherwise physically interconnected, by methods such as weaving, braiding, knitting, knotting, or other comparable methods for interlacing or attaching pre-existing fibers. The term "woven" excludes polymerizing reactions or other types of chemical processing used to create strands of fiber; instead, it focuses on physical manipulation of fibers that have already been created.

As is known to those skilled in the art, different types of weaving and other fiber manipulation create materials having different traits. As one example, conventional cross-weaving generates essentially perpendicular "warp" and "woof" strands that remain nearly linear), while knitting places the fibers in more complex non-linear arrangements; as a result, knitted fabrics typically have a higher level of stretchability and elasticity than cross-woven fabrics. However, if a knitted, braided, or similar fibrous mesh is going to be embedded inside a component such as a hydrogel, the mesh can be "pre-tensioned" to some extent, or it can be treated using a cross-linking or tanning agent, to generate numerous crosslinking bonds throughout the knitted fabric; either approach can be used to stiffen a knitted, braided, or similar mesh. Accordingly, such factors and options should be taken into account in determining the exact form of weaving, knitting, or other interlacing (and any additional tensioning or other finishing or manufacturing steps) that will preferred for a particular type of fiber and/or a particular type of implant.

As used herein, "continuous fibers" can include yarn-like strands, where numerous shorter segments cling together (or have been bonded together, using covalent, ionic, or other molecular attachments) with sufficient avidity and strength to create a larger strand that has sufficient cohesion and tensile strength to allow it to function as a single unitary strand that can be woven into a larger device.

Methods and machines have been developed for carrying out three-dimensional weaving. However, in the prior art, these methods and machines apparently have not been used for creating reinforced hydrogels, for use in surgical implants. Instead, they have been used primarily to create materials and devices used in other fields, such as aerospace and military materials. A company which performs computer-controlled three-dimensional weaving is called Techniweave (Rochester, New Hampshire; its Internet address is www.techniweave.com). It is a subsidiary of Albany International, a producer of machinery for processing paper and other materials.

Based on a site visit to Techniweave by the Applicant herein (a surgeon who specializes in orthopedic and arthroscopic surgery), it is believed that the engineers, researchers, and process developers at Techniweave can adapt their machines and methods to create three-dimensional shapes and sizes that would render them useful as meniscal implants. The Techniweave machines and methods can be adapted to working with most types of fibers having suitable thickness and flexibility, including strands of biologically resorbable polymers as well as non-resorbable biocompatible fibers.

In the second approach to creating a mesh, a set of pre-existing fibers can be formed into a stable three-dimensional mesh by cross-linking, gluing, or similar chemical methods. One such method is similar to the polymerization process described in the Background section, but rather than using monomers that have not yet reacted to form polymeric strands, it will use pre-existing fibers, and a cross-linking agent that will bind the fibers together. For example, strands of a selected type of fiber can be stirred into or otherwise suspended in a solvent that contains a crosslinking agent. Typical crosslinking agents have two reactive groups at the opposed ends of a molecular chain having a desired length; glutaraldehyde offers an example, having reactive aldehyde groups at both ends of a three-carbon chain. Alternately, a crosslinking agent which is branched, or which has a plurality of pendant "side chains" can have more than two reactive groups. Regardless, the mixture of fiber strands and crosslinking agent are suspended together in a solvent, at a concentrations of both agents which will provide a desired final density and three-dimensional structure to the resulting crosslinked mesh. When the crosslinked reaction reaches a desired state of completion in the solvent, the entire suspension is frozen, to preserve the three-dimensional structure of the crosslinked fibers. The solvent is then removed, by a sublimizing (lyophilizing) step, using a vacuum. The crosslinked mesh that remains behind after the solvent has been removed is warmed up, and any quenching, rinsing, or other finishing steps are carried out, to form a completed three-dimensional fibrous mesh.

In the third alternate approach to creating a mesh for use herein, a hydrogel or other elastomeric material can be effectively molded into the shape of a three-dimensional mesh, by using any of several methods. In one method, two monomers are reacted while suspended in a solvent, which is then removed by lyophilization. In an alternate method, a liquid polymer or prepolymer is poured into a mold which will establish the desired three-dimensional mesh, such as with the aid of a layer of salt, sugar, or similar granular material that can be removed by a subsequent solvent treatment. In another alternate method, a liquid polymer or prepolymer is poured into a mold which will establish a three-dimensional mesh, using an "intercalating" or similar solid material that can be subsequently removed by other suitable means (such as heating, etc.). It should be recognized that this type of mesh is not comprised of fibers, per se; instead, it is comprised of a highly porous network of interconnected gaps and interstitial spaces, laced throughout a material that might otherwise be relatively solid.

In the fourth alternate approach to creating a mesh for use herein, a slice of an open-cell foam can be used, as disclosed above. In this method, the relevant physical aspects (including the average pore size, and the thickness of the slice, which can be wedge-shaped if desired) must interact in a cooperative manner to provide a mesh-type structure that will reinforce and strengthen a hydrogel component, if the slice of the foam is embedded within the hydrogel.

The details of these and other suitable manufacturing techniques are known to those skilled in the art. The specific method of manufacturing is not critical to this invention; any suitable manufacturing method that will provide a three-dimensional mesh having desired levels of porosity, density, strength, and other relevant traits can be used. In general, the relevant traits of a mesh component suitable for use as disclosed herein will depend more heavily on the traits (including the diameter, flexibility, and tensile strength) of the fibers (or open-cell foam, etc.) that is selected or chemically created for use herein, than on the method used to form such fibers, foam, etc. into a three-dimensional mesh.

To create an implant for a knee meniscus, the manufacturing procedure must create a three-dimensional mesh which is thicker than just a membrane. As used herein, this implies that a mesh made of fibers must have a thickness of at least 3 layers of fibers (and preferably a substantially larger number of layers), since a relatively thick three-dimensional mesh will promotes better and more stable interlocking of the hydrogel to the mesh than can be achieved with a thin layer of fabric. As currently anticipated, an implantable meniscal device designed for an adult knee will have a thickness of about 15 millimeters (mm) at its thickest point. Since the thickest portion of a meniscal implant is around its periphery, where the implant will be anchored to the walls of the fibrous tissue capsule that surrounds and encloses the knee joint, a mesh component with a thickness that approaches or possibly even exceeds 15 mm, at the peripheral rim, may be able to give greater strength to the implant.

As briefly mentioned above, the "inner surfaces" of a meniscal wedge (these are the surfaces that will rub against femoral and tibial cartilage surfaces, inside a knee joint) should be entirely smooth, so that they will not abrade and damage the femoral and tibial cartilage. Therefore, although the mesh component may be exposed around the peripheral rim of an implant to provide improved anchoring support, the mesh preferably should remain completely hidden, and embedded, beneath any articulating surfaces that will rub against native cartilage.

Since the mesh must remain hidden and covered by a hydrogel, over a large portion of the surface area of a meniscal implant, this design is referred to herein as an "inner-mesh" design.

The "inner-mesh" design of hydrogel implants as disclosed herein offers at least three major advantages over conventional hydrogel implants. The first advantage involves greater strength and durability. These terms imply and include higher levels of any or all of the following: tensile strength, resiliency, resistance to rupture, tearing, leakage, and other loss of integrity, and ability to curtail and limit the size of a tear, cut, or other breach. These advantages arise largely from the fact that in the "inner-mesh" design, an "interpenetrating network" of fibers that pass through the gel itself can be vastly larger and stronger than the essentially "unimolecular" polymeric backbone strands that make up a conventional hydrogel. This is analogous to comparing collagen fiber bundles (which are thick and strong) to proteoglycan filaments (which are so thin they can't be seen even under the most powerful light microscopes).

The second major advantage of the "inner-mesh" design for hydrogel implants arises from the ability of the mesh component, which can be exposed around the peripheral rim of the implant, to provide greatly improved anchoring options and abilities, compared to "naked" hydrogels. Because of various factors (mainly relating to the fact that only about 2 to 5% of their volume is made of fibers, while the rest is water and dissolved molecules), hydrogels typically have low resistance to tearing and cutting. Accordingly, if a strand of suture material is poked and then laced through a hydrogel, it will tend to cut the hydrogel, in a manner comparable to a cheese cutter which uses a wire rather than a blade. It is very difficult and in many cases impossible to adequately anchor (using sutures, pins, etc.) a hydrogel in a manner suited for a permanent implant, unless a reinforcing mesh can also be provided, embedded in the hydrogel.

The third major advantage of the "inner-mesh" design for hydrogel implants arises from the response of surrounding body tissues to a fibrous or other porous structure that is exposed at the surface or positioned around all or a portion of the periphery of the implant. If a fibrous or porous structure is made from a biocompatible polymer or other material, cells from the tissue surrounding the implant will begin growing and proliferating into the mesh, forming a type of scar tissue that is, in effect, intertwined with the mesh. This process of scar tissue formation can be increased by methods known to surgeons, which involving "freshening" the contact surface of the tissue, usually by means of mild abrasion. Accordingly, the resulting ingrowth of cells and tissue into the mesh that is exposed around the periphery of a meniscal implant (or into a porous outer layer of the hydrogel or elastomeric material) can promote and enable a strong, stable, secure, and durable anchoring structure for the implant. If desired, a mesh that is exposed around the peripheral rim of an implant can be coated (using "sputter coating" or similar methods) with calcium-phosphate mixtures that emulate the apatite crystalline structure of bone, to further promote tissue ingrowth into the mesh.

All of these features contribute to the utility, strength, and durability of "inner-mesh" hydrogel implants as disclosed herein, and provide improved fixation and tissue interactions at the interface between the implant and the host tissue.

It should also be recognized that three-dimensional meshes made of fibers can be created using two or more different types of fibers. As one example, thicker fibers might be used around the periphery of a mesh component, to give maximal strength to the periphery and to any anchoring devices. As another example, fibers with clearly defined "hard" surfaces might be used in areas of the mesh that do not pass through the hydrogel component, while other types of fibers with "fuzzy" and/or swellable surfaces might be used to form the fibers that will pass through hydrogel portions. As a third example, a nonstretching fiber might be used to give a high level of strength along an axis, arc, or surface of an implant, while a different type of elastic and/or stretchable fiber might be used to provide flexibility and elastic resilience along a different axis, arc, or surface. As a fourth example, a mesh might be made of both nonresorbable fibers (made of high-strength polymers comparable to nylon) and resorbable fibers (made of collagen or various known polymers) which will gradually be degraded and digested by bodily fluids.

It should also be noted that this invention anticipates any of the following: (i) implants that include living cells in the hydrogel component; (ii) implants that contain only non-biological (i.e., non-cellular) materials in the hydrogel component; and, (iii) implants that may contain more than one hydrogel component.

A number of alternative manufacturing approaches can be used to create a hydrogel device reinforced by a mesh component. Such approaches include the following:

(1) create a complete three-dimensional mesh, then insert a pre-gelled material into it, in a manner that constrains the pre-gelled material to only a certain portion of the mesh, then polymerize that material to form the gel.

(2) create a complete three-dimensional mesh, saturate the entire mesh in a pre-gelled material, cause the material to gel, and then remove gelled material from selected portions of the mesh, by means such as solvents, focused heating, high-pressure spray, etc.

(3) create a gelled or pre-gelled component first, then lace a number of fibrous strands through the gel (such as while the gel is heated to make it softer and more fluid).

(4) create a mesh component, then dip a portion of that component into a gellable material which rests inside a molding device.

(5) fabricate a portion of a mesh component, add a gel component to it by means such as injection or submergence, then fabricate the remainder of the mesh component.

In addition, now that this type of composite device has been disclosed, surgeons are likely to find it adaptable and useful for various types of surgical repair in other joints, such as shoulder or wrist joints (which have meniscus-like tissues), as well as some cases involving damaged ankles or elbows, and possibly even some situations involving damaged hips.

This type of implant is also likely to be useful in surgical repair of damaged or diseased appendages in which multiple bones must interact, such as in the hands and feet. Accordingly, as used herein, the term "joint" refers to an interface between two or more different and distinct bones, in a mammal. As used herein, this term covers the classical joints (including knees, shoulders, wrists, ankles, etc.), as well as the interfaces between bones in an appendage such as a foot or hand. Such uses are likely to require modifications in the size and shape of such implants, to maximize their utility in joints other than knees; however, such modifications can be made easily and directly, based on the teachings herein, using no more than routine experimentation.

Viewed from slightly different perspectives, the implants disclosed herein can also be described in the following terms. In one preferred embodiment, this type of surgically implantable device comprises a hydrogel component and a mesh component, wherein (a) the mesh component provides the implant device with means for securely anchoring the device to tissue which surrounds the joint; and, (b) the hydrogel component provides a smooth and lubricious surface, in at least one surface area (and preferably all surface areas) which will contact and rub against a natural cartilage surface in the joint.

Stated in slightly different terms, the implant devices disclosed herein comprise: (a) a body made of elastomeric material, and a mesh component embedded within the body of the device, wherein at least a portion of said elastomeric material comprises a hydrogel material which retains water molecules that are able to permeate into and out of the hydrogel material; (b) at least one articulating surface made of a smooth and lubricious hydrogel material, wherein each articulating surface is designed to press against at least one bone or cartilage surface following implantation of the device; and, (c) at least one anchoring surface having an exposed porous surface made of material that will promote tissue ingrowth into the porous surface following implantation of the device; and wherein the mesh component embedded within the body of said device is sized and positioned in a manner which: (i) provides a flexible supporting structure beneath at least one articulating surface, which reinforces and strengthens said articulating surface, and (ii) provides a plurality of anchoring accommodations which will reinforce anchoring of the device to surrounding tissue after surgical implantation of the device.

Also disclosed herein is a method of surgically replacing damaged tissue in a mammalian joint, comprising the step of surgically implanting, into the joint, a device comprising a hydrogel component with a reinforcing mesh component as disclosed herein.

Thus, there has been shown and described a new and useful means for creating a surgical implant having a smooth hydrogel surface on at least one exposed surface area, and having a reinforcing mesh component embedded within at least a portion of the hydrogel, to provide improved anchoring and strength. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Ambrosio, L., et al, "Composite hydrogels for implants," *Proc Inst Mech Eng* [H] 212: 93–9 (1998)

Blue, M. A., et al, "In vivo results of hydrogel composite pericardial substitutes," *ASAIO Trans* 37: M152–3 (1991)

Corkhill, P. H., et al, "Synthetic hydrogels. VI. Hydrogel composites as wound dressings and implant materials," *Biomaterials* 10: 3–10 (1989)

Gorman, S. P., et al, "Characterization and assessment of a novel poly(ethylene oxide)/polyurethane composite hydrogel (Aquavene) as a urethral stent biomaterial," *J Biomed Mater Res* 39: 642–9 (1998)

Walker, A. S., et al, "Performance of a hydrogel composite pericardial substitute after long-term implant studies," *ASAIO J* 38: M550–4 (1992)

Wang, N., et al, "A heterogeneously structured composite based on poly(lactic-co-glycolic acid) microspheres and poly(vinyl alcohol) hydrogel nanoparticles for long-term protein drug delivery," *Pharm Res* 16: 1430–5 (1999)

What is claimed is:

1. A non-resorbable Meniscal device designed for surgical emplacement in a mammalian joint, comprising a synthetic non-resorbable hydrogel component and a flexible fibrous mesh component, wherein:
    a. the synthetic non-resorbable hydrogel component provides a smooth and lubricious surface, on at least one surface area which will contact and rub against a natural cartilage surface in the joint;
    b. the flexible fibrous mesh component reinforces the smooth and lubricious surface, and provides reinforced means for anchoring the device to tissue which surrounds the joint, and extends throughout essentially all of the hydrogel component other than one or more smooth surfaces,
    and wherein the device is non-resorbable, and is designed for surgical implantation without cells embedded within the hydrogel component.

2. The non-resorbable device of claim 1, having a size and shape which render the device suitable for implantation in a human knee joint to replace a damaged meniscus, wherein the device:
    a. has a first smooth and lubricious surface designed to articulate against femoral cartilage,
    b. has a second smooth and lubricious surface designed to articulate against tibial cartilage, and,
    c. has a peripheral surface designed to enable secure anchoring of the device to tissue surrounding a knee joint.

3. The device of claim 1, having a size and shape which render the device suitable for implantation in a joint selected from the group consisting of shoulders, wrists, ankles, and elbows.

4. The device of claim 1, having a size and shape which render the device suitable for implantation in an appendage selected from the group consisting of feet and hands.

5. The device of claim 1, having a first relatively soft hydrogel portion which provides a lubricious surface on at least one surface area of the device, and having a second hydrogel portion which has greater hardness and stiffness in at least one portion of the device.

6. The device of claim 1, having a hydrogel portion which provides a lubricious surface on at least one surface area of the device, and having at least one interior portion comprising an elastomeric material which is not a hydrogel.

7. A non-resorbable meniscal device for surgical implantation, comprising:
    a. a body made of elastomeric material, and a flexible fibrous mesh component embedded within the body of the device, wherein at least a portion of said elastomeric material comprises a hydrogel material which retains water molecules that are able to permeate into and out of the hydrogel material;
    b. at least one articulating surface made of a smooth and lubricious synthetic non-resorbable hydrogel material, wherein the articulating surface is designed to press against at least one bone or cartilage surface following implantation of the device, and, c. at least one anchoring surface having an exposed porous surface, made of fibrous mesh material that will promote tissue ingrowth into the porous surface following implantation of the device;

and wherein the flexible fibrous mesh component embedded within the body of said device is sized and positioned in a manner which: (i) provides a flexible supporting structure beneath at least one articulating surface, which reinforces and strengthens said articulating surface, and (ii) provides an anchoring accommodation which will reinforce anchoring of the device to surrounding tissue after surgical implantation of the device, and wherein the non-resorbable device is designed for surgical implantation without embedded cells.

8. The non-resorbable device of claim 7, having a size and shape which render the device suitable for implantation in a human knee joint to replace a damaged meniscus, wherein the device:

a. has a first smooth and lubricious surface designed to articulate against femoral cartilage, b. has a second smooth and lubricious surface designed to articulate against tibial cartilage, and, c. has a peripheral surface designed to enable secure anchoring of the device to tissue surrounding a knee joint.

9. The device of claim 7, having a size and shape which render the device suitable for implantation in a joint selected from the group consisting of shoulders, wrists, ankles, and elbows.

10. The device of claim 7, having a size and shape which render the device suitable for implantation in an appendage selected from the group consisting of feet and hands.

11. The device of claim 7, having a first relatively soft hydrogel portion which provides a lubricious surface on at least one articulating surface of the device, and having a second hydrogel portion which has greater hardness and stiffness in an interior portion of the device.

12. The device of claim 7, having a hydrogel portion which provides a lubricious surface on at least one articulating surface of the device, and having at least one interior portion comprising an elastomeric material which is not a hydrogel.

13. A non-resorbable device for surgical implantation to replace meniscal tissue in a joint, comprising a body made of elastomeric material with a reinforcing flexible fibrous mesh, and having:

a. a first smooth and lubricious hydrogel articulating surface designed to articulate against femoral cartilage;

b. a second smooth and lubricious surface designed to articulate against tibial cartilage, and, c. at least one anchoring surface having exposed pores that will promote tissue ingrowth into the exposed pores following implantation of the device, wherein the reinforcing flexible fibrous mesh extends throughout essentially all of the elastomeric material except for a first coating layer which provides the first smooth and lubricious articulating surface, and a second coating layer which provides the second smooth and lubricious articulating surface, and wherein the non-resorbable device is designed for surgical implantation without cells embedded within the device.

14. A method of surgically replacing damaged meniscal tissue in a mammalian joint, comprising the step of surgically implanting, into the joint, a non-resorbable device comprising a synthetic non-resorbable hydrogel component and a flexible fibrous mesh component, wherein:

a. the mesh component extends throughout essentially all of the hydrogel component other than one or more smooth surfaces, and provides the non-resorbable device with means for securely anchoring the device to tissue which surrounds the joint; and, b. the hydrogel component provides a smooth and lubricious surface, in a first surface area which will contact and rub against a femoral cartilage surface in the joint, and in a second surface area which will contact and rub against a tibial cartilage surface in the joint and wherein the non-resorbable device is designed for surgical implantation without cells embedded therein.

15. The method of claim 14, wherein the device has a first relatively soft hydrogel portion which provides a lubricious surface on at least one articulating surface of the device, and a second hydrogel portion which has greater hardness and stiffness in an interior portion of the device.

16. The method of claim 14, wherein the non-resorbable device has a first hydrogel portion which provides a lubricious surface on at least one articulating surface of the device, and at least one interior portion comprising an elastomeric material which is not a hydrogel.

17. A method of surgically replacing damaged meniscal tissue in a mammalian joint, comprising the step of surgically implanting, into the joint, a non-resorbable device comprising an elastomeric body component and a flexible fibrous mesh component embedded within the elastomeric body component, wherein the elastomeric body component is provided with:

a. a first smooth and lubricious hydrogel articulating surface designed to articulate against femoral cartilage; and, b. a second smooth and lubricious surface designed to articulate against tibial cartilage, and, c. at least one anchoring surface made of a porous material that will promote tissue ingrowth into the porous material following implantation of the device;

and wherein the mesh component embedded within the elastomeric body component is sized and positioned in a manner which: (i) provides a flexible supporting structure beneath at least one articulating surface, which reinforces and strengthens said articulating surface, (ii) provides a plurality of fibrous anchoring accommodations, which will reinforce anchoring of the device to surrounding tissue after surgical implantation of the device, and (iii) extends throughout essentially all of the elastomeric body component other than the first and second smooth and lubricious surfaces, and wherein the non-resorbable device is designed for surgical implantation without cells embedded therein.

18. The method of claim 17, wherein the device has a first relatively soft hydrogel portion which provides a lubricious surface on at least one articulating surface of the device, and a second hydrogel portion which has greater hardness and stiffness in an interior portion of the device.

19. The method of claim 17, wherein the device has a first hydrogel portion which provides a lubricious surface on at least one articulating surface of the device, and at least one interior portion comprising an elastomeric material which is not a hydrogel.

* * * * *